(12) United States Patent
Jackson

(10) Patent No.: US 10,617,447 B2
(45) Date of Patent: *Apr. 14, 2020

(54) DYNAMIC STABILIZATION MEMBER WITH MOLDED CONNECTION

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/964,520

(22) Filed: Apr. 27, 2018

(65) Prior Publication Data

US 2018/0243008 A1  Aug. 30, 2018

Related U.S. Application Data

(63) Continuation of application No. 15/664,978, filed on Jul. 31, 2017, now Pat. No. 9,956,002, which is a continuation of application No. 15/237,257, filed on Aug. 15, 2016, now Pat. No. 9,750,540, which is a continuation of application No. 14/642,960, filed on Mar. 10, 2015, now Pat. No. 9,439,683, which is a continuation of application No. 12/931,161, filed on Jan. 26, 2011, now Pat. No. 9,101,404, which is a continuation of application No. 12/008,067, filed on Jan. 8, 2008, now Pat. No. 7,901,437.

(60) Provisional application No. 60/897,723, filed on Jan. 26, 2007.

(51) Int. Cl.
*A61B 17/70* (2006.01)

(52) U.S. Cl.
CPC ........ *A61B 17/7031* (2013.01); *A61B 17/701* (2013.01); *A61B 17/7032* (2013.01); *A61B 17/7037* (2013.01); *A61B 17/705* (2013.01); *A61B 17/7008* (2013.01)

(58) Field of Classification Search
CPC .............. A61B 17/7031; A61B 17/701; A61B 17/7032; A61B 17/7037; A61B 17/7008; A61B 17/705
USPC .................................................. 606/246-289
See application file for complete search history.

(56) References Cited

U.S. PATENT DOCUMENTS

| 5,171,279 | A  | 12/1992 | Mathews |
| D346,217 | S  | 4/1994 | Sparker et al. |
| 5,569,253 | A  | 10/1996 | Farris et al. |
| 6,132,431 | A  | 10/2000 | Nilsson et al. |
| 6,251,112 | B1 | 6/2001 | Jackson |
| 6,290,700 | B1 | 9/2001 | Schmotzer |

(Continued)

OTHER PUBLICATIONS

U.S. Appl. No. 15/918,181, filed Mar. 12, 2018, Jackson.
U.S. Appl. No. 16/543,235, filed Aug. 16, 2019, Jackson.

*Primary Examiner* — Pedro Philogene
(74) *Attorney, Agent, or Firm* — Polsinelli PC

(57) ABSTRACT

A dynamic fixation medical implant having at least two bone anchors includes a longitudinal connecting member assembly having at least one transition portion and cooperating outer sleeve, both the transition portion and sleeve being disposed between the two bone anchors. The transition portion includes a rigid length or rod having apertures therein and a molded plastic length that extends through the apertures, thus attaching the plastic length to the rigid length. The sleeve surrounds the transition portion and extends between the pair of bone anchors, the sleeve being compressible in a longitudinal direction between the bone anchors.

11 Claims, 4 Drawing Sheets

(56) References Cited

U.S. PATENT DOCUMENTS

| | | |
|---|---|---|
| 6,565,565 B1 | 5/2003 | Yuan et al. |
| 6,997,927 B2 | 2/2006 | Jackson |
| 7,713,288 B2 | 5/2010 | Timm et al. |
| 7,815,665 B2 | 10/2010 | Jahng et al. |
| 7,828,825 B2 | 11/2010 | Bruneau et al. |
| 7,842,072 B2 | 11/2010 | Dawson |
| 7,901,437 B2* | 3/2011 | Jackson ............... A61B 17/701 606/278 |
| 7,988,710 B2 | 8/2011 | Jahng et al. |
| 8,029,544 B2 | 10/2011 | Hested et al. |
| 8,114,133 B2 | 2/2012 | Logan |
| 8,128,667 B2 | 3/2012 | Jackson |
| 8,157,843 B2 | 4/2012 | Biederman et al. |
| 8,292,926 B2 | 10/2012 | Jackson |
| 8,366,745 B2 | 2/2013 | Jackson |
| 8,465,526 B2 | 6/2013 | Friedrich et al. |
| 9,101,404 B2* | 8/2015 | Jackson ............... A61B 17/701 |
| 9,439,683 B2* | 9/2016 | Jackson ............... A61B 17/701 |
| 9,451,989 B2 | 9/2016 | Jackson |
| 9,668,771 B2 | 6/2017 | Jackson |
| 9,750,540 B2* | 9/2017 | Jackson ............... A61B 17/701 |
| 9,861,394 B2 | 1/2018 | Jackson |
| 9,931,139 B2 | 4/2018 | Jackson |
| 9,956,002 B2* | 5/2018 | Jackson ............... A61B 17/701 |
| 10,130,393 B2 | 11/2018 | Jackson |
| 2002/0035366 A1 | 3/2002 | Walder et al. |
| 2002/0055740 A1 | 5/2002 | Lieberman |
| 2002/0107570 A1 | 8/2002 | Sybert et al. |
| 2002/0116001 A1 | 8/2002 | Schafer |
| 2002/0116065 A1 | 8/2002 | Jackson |
| 2002/0198526 A1 | 12/2002 | Shaolian et al. |
| 2003/0083657 A1 | 5/2003 | Drewry et al. |
| 2003/0212398 A1 | 11/2003 | Jackson |
| 2004/0049190 A1 | 3/2004 | Biederman et al. |
| 2004/0138662 A1 | 7/2004 | Landry et al. |
| 2004/0143265 A1 | 7/2004 | Landry et al. |
| 2004/0167523 A1 | 8/2004 | Jackson |
| 2004/0172032 A1 | 9/2004 | Jackson |
| 2004/0215191 A1 | 10/2004 | Kitchen |
| 2004/0236327 A1 | 11/2004 | Paul et al. |
| 2004/0236328 A1 | 11/2004 | Paul et al. |
| 2005/0010220 A1* | 1/2005 | Casutt ............... A61B 17/7008 606/86 A |
| 2005/0085815 A1 | 4/2005 | Harms et al. |
| 2005/0131407 A1 | 6/2005 | Sicvol et al. |
| 2005/0149020 A1 | 7/2005 | Jahng |
| 2005/0203514 A1 | 9/2005 | Jahng et al. |
| 2005/0203517 A1 | 9/2005 | Jahng et al. |
| 2005/0277919 A1 | 12/2005 | Slivka et al. |
| 2005/0277920 A1 | 12/2005 | Slivka et al. |
| 2005/0277922 A1 | 12/2005 | Trieu et al. |
| 2005/0277932 A1 | 12/2005 | Farris |
| 2005/0288671 A1 | 12/2005 | Yuan et al. |
| 2005/0288672 A1 | 12/2005 | Ferree |
| 2006/0025767 A1 | 2/2006 | Khalili |
| 2006/0036240 A1 | 2/2006 | Colleran et al. |
| 2006/0058788 A1 | 3/2006 | Hammer et al. |
| 2006/0064090 A1 | 3/2006 | Park |
| 2006/0079894 A1 | 4/2006 | Colleran et al. |
| 2006/0142760 A1 | 6/2006 | McDonnell |
| 2006/0149238 A1 | 7/2006 | Sherman et al. |
| 2006/0241602 A1 | 10/2006 | Jackson |
| 2006/0241769 A1 | 10/2006 | Gordon et al. |
| 2006/0247635 A1 | 11/2006 | Gordon et al. |
| 2006/0247779 A1 | 11/2006 | Gordon et al. |
| 2006/0264937 A1 | 11/2006 | White |
| 2007/0005063 A1 | 1/2007 | Bruneau et al. |
| 2007/0032123 A1 | 2/2007 | Timm et al. |
| 2007/0100341 A1 | 5/2007 | Reglos et al. |
| 2007/0118123 A1 | 5/2007 | Strausbaugh et al. |
| 2007/0123864 A1 | 5/2007 | Walder et al. |
| 2007/0129729 A1* | 6/2007 | Petit ............... A61B 17/7022 606/254 |
| 2007/0191841 A1 | 8/2007 | Justis et al. |
| 2007/0233064 A1 | 10/2007 | Holt |
| 2007/0233075 A1 | 10/2007 | Dawson |
| 2007/0270821 A1 | 11/2007 | Trieu et al. |
| 2007/0270840 A1 | 11/2007 | Chin et al. |
| 2007/0276380 A1 | 11/2007 | Jahng et al. |
| 2007/0288011 A1 | 12/2007 | Logan |
| 2008/0021469 A1 | 1/2008 | Holt |
| 2008/0051787 A1 | 2/2008 | Remington et al. |
| 2008/0086125 A1 | 4/2008 | Molz et al. |
| 2008/0086130 A1 | 4/2008 | Lake |
| 2008/0161857 A1 | 7/2008 | Hestad et al. |
| 2008/0183213 A1 | 7/2008 | Veldman et al. |
| 2008/0234691 A1 | 9/2008 | Schwab |
| 2008/0234737 A1 | 9/2008 | Boschert |
| 2008/0234744 A1 | 9/2008 | Zylber et al. |
| 2008/0262551 A1 | 10/2008 | Rice et al. |
| 2008/0262553 A1 | 10/2008 | Hawkins et al. |
| 2008/0275504 A1 | 11/2008 | Bonin et al. |
| 2008/0294198 A1 | 11/2008 | Jackson |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0036924 A1 | 2/2009 | Egli et al. |
| 2009/0054932 A1 | 2/2009 | Butler et al. |
| 2009/0082815 A1 | 3/2009 | Zylber et al. |
| 2009/0088799 A1 | 4/2009 | Yeh |
| 2009/0093846 A1* | 4/2009 | Hestad ............... A61B 17/7008 606/255 |
| 2009/0099606 A1 | 4/2009 | Hestad et al. |
| 2009/0105757 A1 | 4/2009 | Gimbel et al. |
| 2009/0105758 A1 | 4/2009 | Gimbel et al. |
| 2009/0177231 A1 | 7/2009 | Kiester |
| 2009/0198280 A1 | 8/2009 | Spratt et al. |
| 2009/0204152 A1 | 8/2009 | Blain |
| 2009/0228045 A1 | 9/2009 | Hayes et al. |
| 2009/0240285 A1 | 9/2009 | Friedrich et al. |
| 2009/0240286 A1 | 9/2009 | Friedrich et al. |
| 2009/0259257 A1 | 10/2009 | Prevost |
| 2009/0275983 A1 | 11/2009 | Veldman et al. |
| 2009/0299411 A1 | 12/2009 | Laskowitz et al. |
| 2010/0010542 A1 | 1/2010 | Jackson |
| 2010/0010543 A1 | 1/2010 | Jackson |
| 2010/0036423 A1 | 2/2010 | Hayes |
| 2010/0137912 A1 | 6/2010 | Alcock et al. |
| 2010/0174319 A1 | 7/2010 | Jackson |
| 2010/0211105 A1 | 8/2010 | Moumene et al. |
| 2010/0228292 A1 | 9/2010 | Arnold et al. |
| 2010/0331887 A1 | 12/2010 | Jackson et al. |
| 2011/0301644 A1 | 12/2011 | Belliard |
| 2012/0035660 A1 | 2/2012 | Jackson |
| 2012/0053636 A1 | 3/2012 | Schmocker |
| 2012/0221054 A1 | 8/2012 | Jackson |
| 2013/0123853 A1 | 5/2013 | Seme et al. |
| 2013/0197582 A1 | 8/2013 | Prevost et al. |
| 2014/0018857 A1 | 1/2014 | Jackson |
| 2014/0039555 A1 | 2/2014 | Jackson |
| 2014/0222076 A1 | 8/2014 | Jackson |
| 2014/0343610 A1 | 11/2014 | Jackson |
| 2014/0379030 A1 | 12/2014 | Jackson |
| 2015/0216567 A1 | 8/2015 | Trautwein et al. |
| 2015/0230827 A1 | 8/2015 | Zylber et al. |
| 2015/0320449 A1 | 11/2015 | Jackson |
| 2016/0310169 A1 | 10/2016 | Jackson et al. |
| 2016/0354118 A1 | 12/2016 | Belliard et al. |
| 2017/0100165 A1 | 4/2017 | Jackson |
| 2017/0231662 A1 | 8/2017 | Jackson |
| 2018/0132901 A1 | 5/2018 | Jackson et al. |
| 2018/0168693 A1 | 6/2018 | Jackson et al. |
| 2018/0185068 A1 | 7/2018 | Jackson |
| 2018/0221063 A1 | 8/2018 | Jackson |
| 2019/0183534 A1 | 6/2019 | Jackson |

* cited by examiner

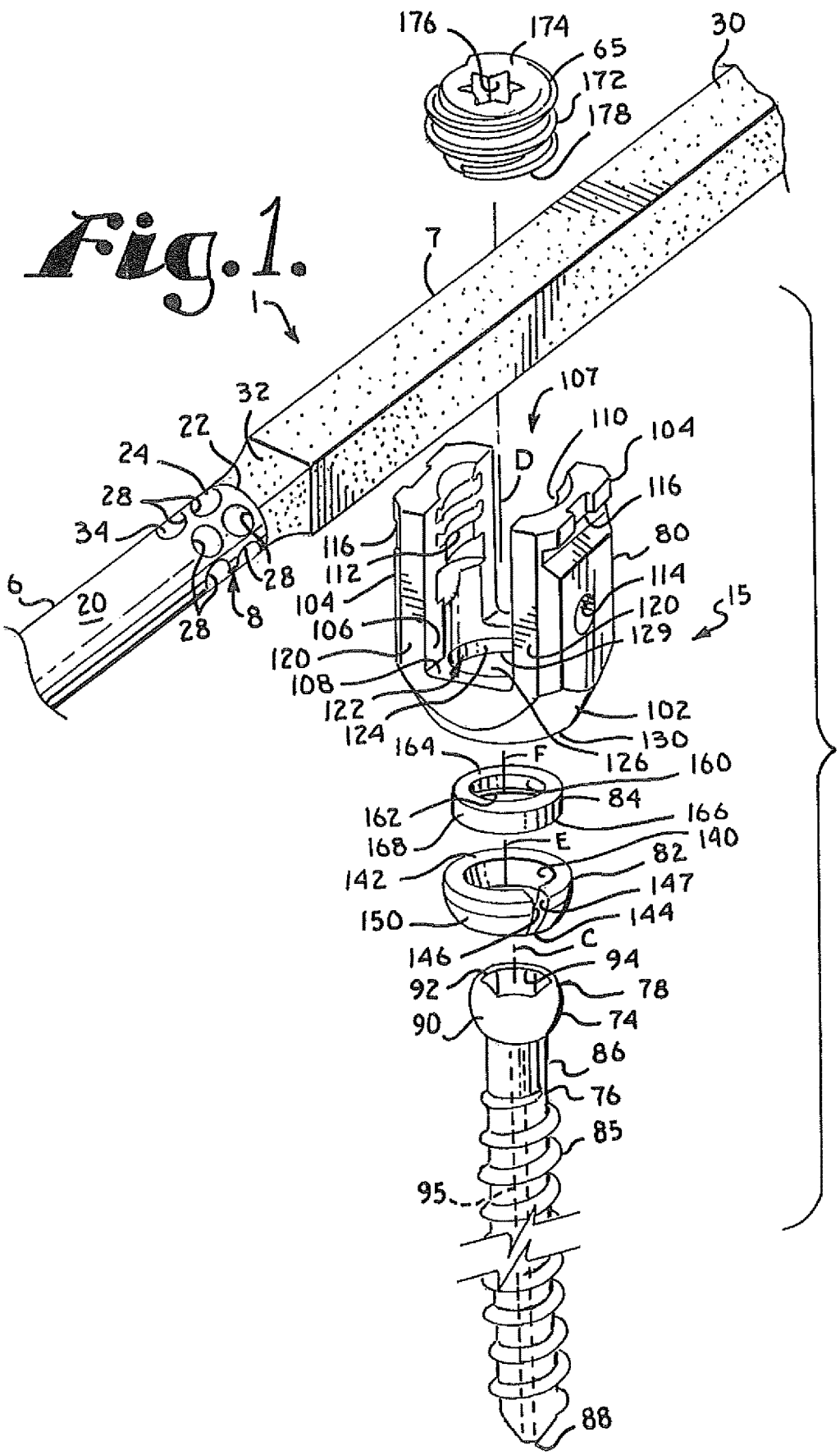

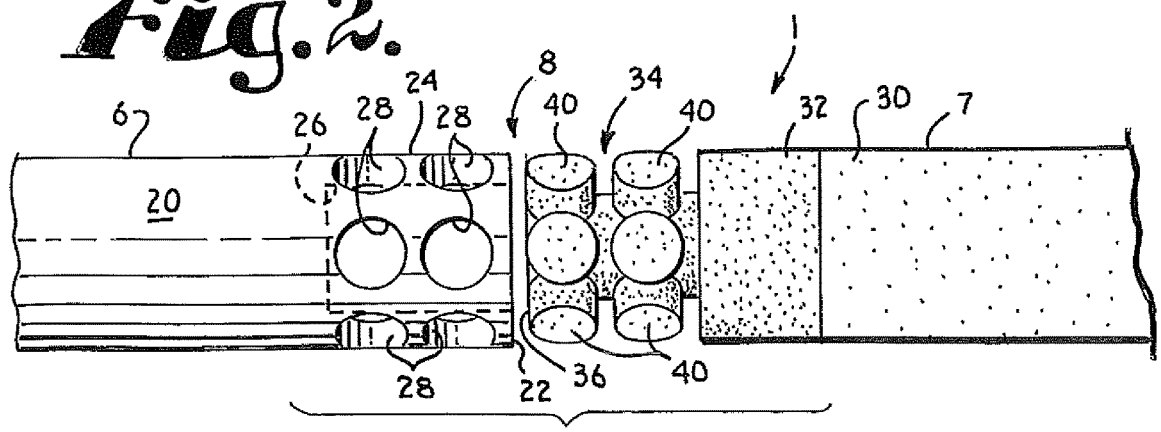
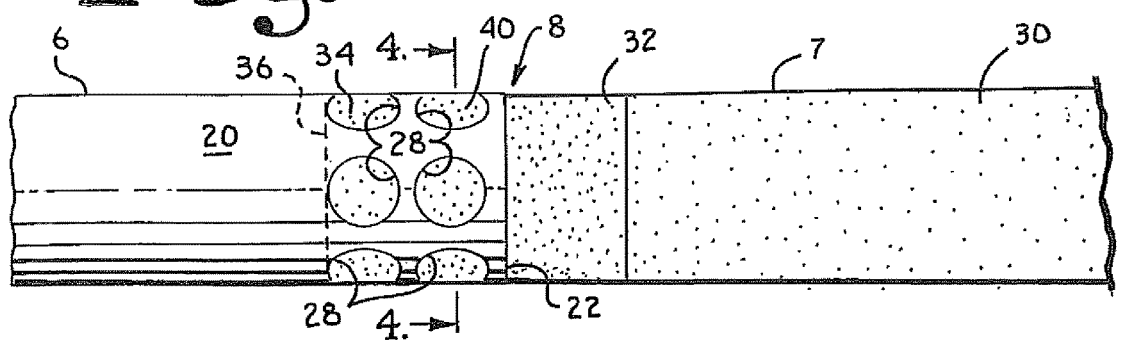
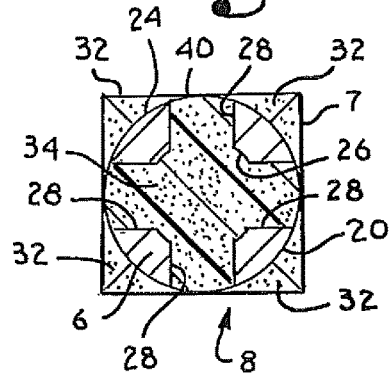

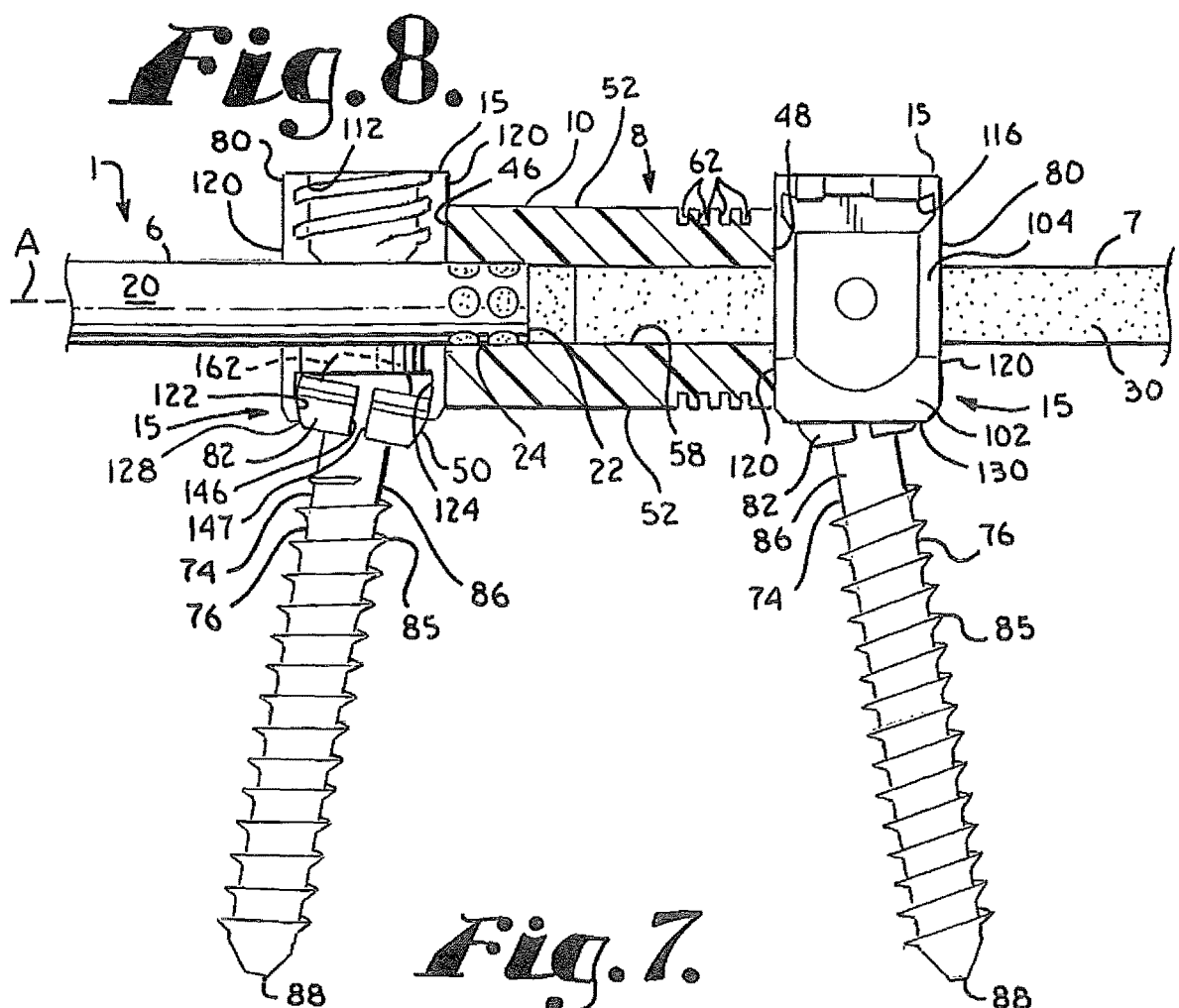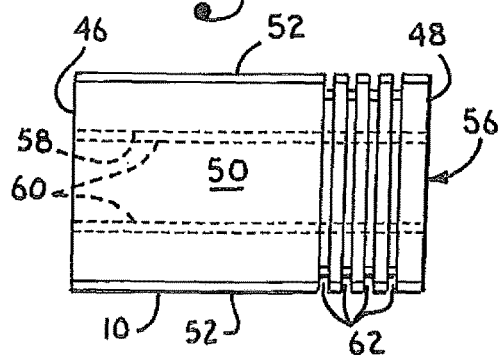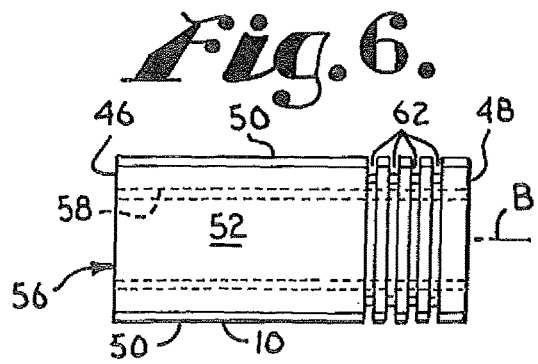

DYNAMIC STABILIZATION MEMBER WITH MOLDED CONNECTION

CROSS REFERENCE TO RELATED APPLICATIONS

This application is a continuation of U.S. patent application Ser. No. 15/664,978, filed Jul. 31, 2017, which is a continuation of U.S. patent application Ser. No. 15/237,257, filed Aug. 15, 2016, now U.S. Pat. No. 9,750,540, which is a continuation of U.S. patent application Ser. No. 14/642,960, filed Mar. 10, 2015, now U.S. Pat. No. 9,439,683, which is a continuation of U.S. patent application Ser. No. 12/931,161, filed Jan. 26, 2011, now U.S. Pat. No. 9,101,404, which is a continuation of U.S. patent application Ser. No. 12/008,067, filed Jan. 8, 2008, now U.S. Pat. No. 7,901,437, which claims the benefit of U.S. Provisional Application No. 60/897,723, filed Jan. 26, 2007. Each of these applications is incorporated by reference in its entirety herein for all purposes.

BACKGROUND

The present invention is directed to dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, is not always desirable. An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized bone anchors and tooling for tensioning and holding the chord or strand in the bone anchors. Although flexible, the cords or strands utilized in such systems do not allow for elastic distraction or stretchability of the system once implanted because the cord or strand must be stretched or pulled to maximum tension in order to provide a stable, supportive system.

The complex dynamic conditions associated with spinal movement make it a challenge to design flexible and/or elastic elongate longitudinal connecting members that exhibit an adequate fatigue strength to provide stabilization and protected motion of the spine, without fusion, and allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protected movement.

SUMMARY

Longitudinal connecting member assemblies according to the invention for use between at least two bone anchors provide dynamic, protected motion of the spine and may be extended to provide additional dynamic sections or more rigid support along an adjacent length of the spine, with fusion, if desired. According to the invention, an elongate molded plastic structure, such as an elastomer is fixed to an end portion of an elongate rigid portion by molding or other fixing processes, including, but not limited to chemical bonding, blending, or surface adherence. For example, in an embodiment of the invention, molded plastic is disposed within a plurality of through bores of the end portion of a rigid rod. A longitudinal connecting member assembly according to the invention thus includes a transition or connection portion that is placed between a pair of bone anchors, the transition portion having a first substantially solid rigid portion and a second molded portion having at least some elasticity. A sleeve or spacer surrounds the juncture of the first and second portions at the transition portion. The sleeve extends between the pair of bone anchors and is in contact therewith. The transition portion and the outer sleeve cooperate dynamically, both features having some flexibility, with the outer sleeve primarily protecting and limiting flexing movement of the inner transition portion. The outer sleeve may include a grooved portion that may be compressed upon installation between two bone anchors.

Embodiments include, for example, a substantially solid rigid first portion, such as a metal rod having a plurality of apertures formed near an end thereof. A second solid elastic rod portion is fabricated by a molding process wherein the elastic rod portion is formed adjacent the metal rod portion such that the plastic polymer forming the elastic rod portion also flows into the apertures of the metal rod thereby fixing the first and second portions to one another.

A variety of embodiments according to the invention are possible. For example, cylindrical rods, bars of square or rectangular cross-section, or other substantially rigid structures having different measures of rigidity may be connected with flexible rods or bars of varying stiffness and elasticity according to embodiments of the invention. Either rigid portions or flexible portions may be of greater or lesser lengths for attaching to one or up to a plurality of bone anchors.

OBJECTS AND ADVANTAGES

Therefore, it is an object of the present invention to provide dynamic medical implant stabilization assemblies having longitudinal connecting members that include both rigid and more flexible sections or lengths, the flexible sections allowing for at least one of bending, torsion, compression and distraction of the assembly. Another object of the invention is to provide such an assembly wherein the flexible section or sections are insertable into a protective outer sleeve. A further object of the invention is to provide such an assembly wherein the outer sleeve may be compressed upon installation. A further object of the invention is to provide dynamic medical implant longitudinal connecting members that may be utilized with a variety of bone screws, hooks and other bone anchors. Another object of the invention is to provide a more rigid or solid connecting member portion or segment, if desired, such as a solid rod portion integrally linked to one or more flexible portions or segments. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged and partial exploded perspective view of a polyaxial bone screw and cooperating dynamic longitudinal connecting member according to the invention (shown without the sleeve of FIG. 5).

FIG. 2 is an enlarged and partial exploded front elevational view of the dynamic longitudinal connecting member of FIG. 1.

FIG. 3 is an enlarged and partial front elevational view of the dynamic longitudinal connecting member of FIG. 1.

FIG. 4 is a cross-sectional view taken along the line 4-4 of FIG. 3.

FIG. 5 is an enlarged front elevational view of the sleeve or spacer for the dynamic longitudinal connecting member of FIG. 1.

FIG. 6 is a top plan view of the spacer of FIG. 5.

FIG. 7 is a side elevational view of the spacer of FIG. 5.

FIG. 8 is an enlarged and partial front elevational view of the longitudinal connecting member of FIG. 1, the spacer of FIG. 5 and shown with two polyaxial bone screws of FIG. 1, with portions broken away to show the detail thereof.

DETAILED DESCRIPTION

Figure 9:
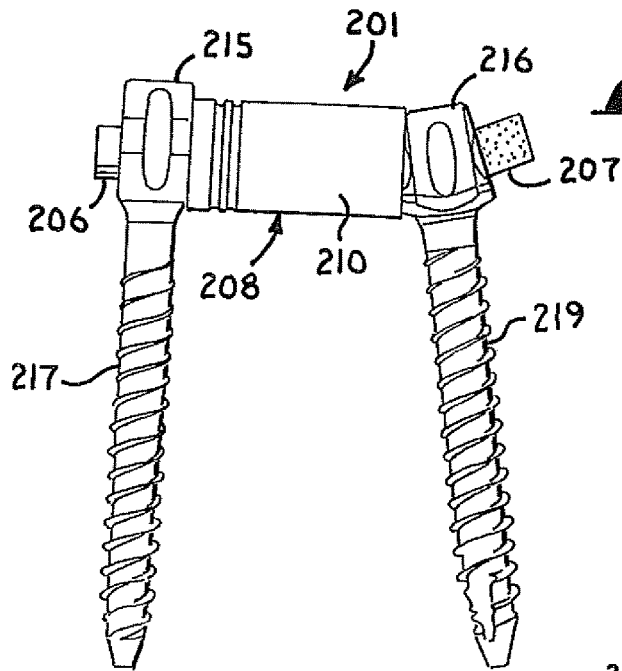
FIG. 9 is an enlarged front elevational view a second embodiment of a dynamic longitudinal connecting member according to the invention shown assembled with a fixed open screw and a fixed closed screw.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-8, the reference numeral 1 generally designates a dynamic stabilization longitudinal connecting member assembly according to the present invention. The connecting member assembly 1 is elongate, having a central axis A and generally includes a first rigid member 6, a second more flexible, elastomeric member 7 and a central, dynamic connection or transition portion or segment 8 disposed at and near a juncture of the members 6 and 7. The transition portion or segment 8 is receivable in a spacer or sleeve 10 with the sleeve 10 ultimately in position about the segment 8 when the assembly 1 is operatively assembled with at least a pair of bone screw assemblies 15 as illustrated in FIG. 8. The bone screw assembly, generally 15, that may be used with longitudinal connecting member assemblies 1 of the invention is also illustrated in FIG. 1.

The rigid member 6 is typically a substantially solid structure, such as the illustrated solid rod having an outer cylindrical surface 20. The rigid member 6 further includes an end 22 that is hollowed out and/or includes a plurality of through bores or apertures. In the illustrated embodiment, a rod portion 24 adjacent to the end 22 is substantially tubular, having an inner cylindrical surface 26 and a plurality of through apertures or through bores 28 running through and being open at both the outer surface 20 and the inner surface 26.

The elastomeric member 7 in the illustrated embodiment is substantially bar-shaped, having an elongate portion 30 with a substantially square cross-section, a tapered portion 32 and a rigid member connection portion 34. The connection portion 34 is disposed near an end 36 of the member 7. As illustrated in FIG. 4, the elongate portion 30 has a width measured at the cross-section that is substantially the same as a diameter of the cylindrical member 6, with the tapered portion 32 gradually providing the minor transition in shape from the bar shape of the elongate portion 30 of the member 7 to the cylindrical shape of the portion 24 of the member 6. The portions 30, 32 and 34 are integral and preferably fabricated by molding the member 7 in the presence of and adjacent to the rigid member 6 so that the portion 34 flows into a void defined by the inner cylindrical surface 26 as the portions 30 and 32 are also molded, with the portion 34 further flowing through each of the apertures 28 of the rigid member 6. It is also foreseen that in certain embodiments, the portion 34 may be fabricated separately from the rigid member 6 with flexible protrusions 40 of the portion 34 being sized and shaped (such as by separate mold or machining) for being received within the apertures 28 of the rigid member 6 when the end 36 of the elastomeric member 7 is inserted into the rigid member 6 at the end 22.

Figure 10:
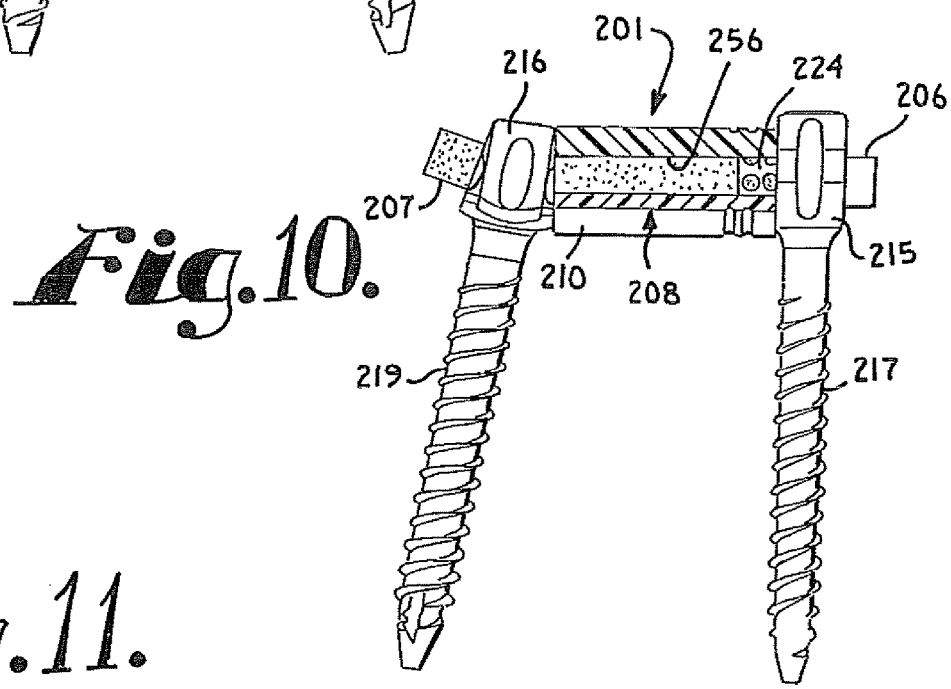
FIG. 10 is a rear elevational view of the assembly of FIG. 9 with portions broken away to show the detail thereof.
Figure 11:
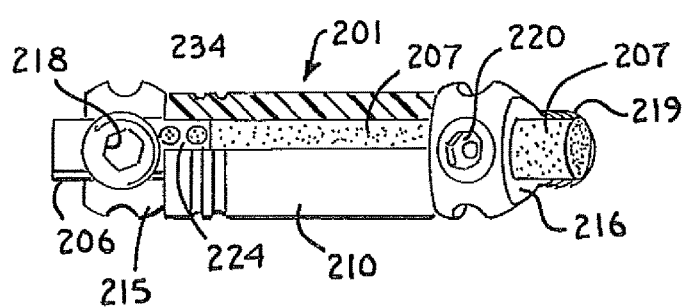
FIG. 11 is a top plan view of the assembly of FIG. 9 with portions broken away to show the detail thereof.

It is foreseen that each of the members 6 and 7 may be cylindrical in shape as illustrated in the embodiment shown in FIGS. 9-11. It is also foreseen that one or both of the members 6 and 7 may have other forms, including but not limited to oval, square and rectangular cross-sections as well as other curved or polygonal shapes, the members 6 and 7 having the same or different cross-sections. The members 6 and 7 are each of a length for cooperating with at least one and up to a plurality of bone attachment members, such as bone screws 15, other bone screws as will be described below, or hooks. The rigid member 6 is made from metal, metal alloys or other suitable materials, including plastic polymers such as polyetheretherketone (PEEK), ultra-high-molecular weight-polyethylene (UHMWP), polyurethanes and composites. The elastomeric member 7 is made from natural or synthetic elastomers, including, but not limited to polyisoprene (natural rubber), and synthetic polymers, copolymers, and thermoplastic elastomers, and mixtures thereof, with the illustrated member 7 being a polyurethane elastomer. The illustrated sleeve 10 is also preferably made from a plastic, such as a thermoplastic elastomer, for example, polyethylene or polycarbonate-urethane having a greater stiffness than the elastomer of the member 7. In order to have low or no wear debris, the sleeve 10 inner surfaces and/or outer surfaces of cooperating portions of members 6 and 7 may be coated with an ultra thin, ultra hard, ultra slick and ultra smooth coating, such as may be obtained from ion bonding techniques and/or other gas or chemical treatments. It is foreseen that the member 7 may be sized and made from such materials as to provide for a relatively more rigid assembly 1 or a relatively more flexible assembly 1 with respect to flex or bendability along the transition portion 8 and the portion 30. Furthermore, when the portion 30 is elongate, sleeves 10 are preferably disposed between bone screws along such length. Also, since the distance between the bone screws can vary, the member 7 may need to be more or less stiff.

With particular reference to FIGS. 5-8, the sleeve or spacer 10 is a part of the assembly 1 that advantageously cooperates with the mid section or transition portion 8 of the assembly 1, providing limitation and protection of movement of the section 8. The sleeve 10 also protects patient body tissue from damage that might otherwise occur in the vicinity of the juncture of the rigid member 6 and elastomeric member 7. Thus, the sleeve 10 is sized and shaped for substantially even and precise alignment and substantial contact between flat end faces 46 and 48 of the sleeve 10 and cooperating flat side surfaces of the bone screws 15 as will be described in greater detail below. Furthermore, as will be discussed in greater detail below, in certain embodiments according to the invention, when the sleeve 10 is implanted, and the bone screw assemblies 15 are tightened into a locked position with respect to the longitudinal connecting member assembly 1, the tools utilized to implant the assembly 1 and/or the bone screws 15 may be manipulated so as to axially compress the sleeve 10 between facing surfaces of adjacent bone screws 15. Such compression during installation results in some tension and/or distraction of the member 7 located between the bone screws 15 when the implantation tools are removed from the bone screws 15, as the sleeve surfaces 46 and 48 then press against the facing bone screw surfaces, but the connection portion 8 is otherwise fixed with respect to each of the bone screws 15. Such dynamic tension/compression relationship between the sleeve 10 and the central connection portion 8 provides further strength and stability to the overall assembly and also allows for the entire connecting member assembly 1 disposed between the bone screws 15 to elongate, if needed, in response to spinal movement. The increased stability and strength of the assembly advantageously allows for use of a smaller, more compact, reduced volume, lower profile longitudinal connecting member assembly 1 and cooperating bone anchors than, for example, flexible cord and spacer type longitudinal connecting member assemblies.

The illustrated sleeve 10 has an outer rectangular cross-section with opposed sides or side surfaces 50 and a pair of opposed anterior/posterior sides or surfaces 52. Each of the surfaces 50, 52 extend between the flat end faces 46 and 48. The geometry of the sleeve 10 allows for a narrower width between the parallel surfaces 50 than a distance between the surfaces 52. Such geometry provides adequate stiffness or support for the flexible member 7 at the segment 8 in flexing due to the greater distance between the posterior/anterior curved surfaces 52, while the more narrow width or distance between the flat surfaces 50 allows for placement of the sleeve 10 between adjacent vertebrae without engagement with such vertebrae. Stated in another way, a cylindrical sleeve having a diameter large enough to produce a desired limit of bending or flexing movement of the member 7 at the central or transition portion 8 would most likely have a diameter large enough to result in interference of the sleeve cylindrical surface with portions of adjacent vertebrae. The rectangular cross-section of the sleeve 10 allows allow for adequate clearance but do not detract from an overall strength of the sleeve 10.

Extending along a substantially central axis B of the sleeve 10 (that corresponds to the axis A when the transition portion 8 is disposed in the sleeve 10) is an internal channel or bore 56 of substantially square cross-section. The surfaces 58 defining the bore 56 are sized and shaped to slidingly receive the members 6 and 7, with chamfers 60 located at corners defining the bore 56 to provide ease in receiving the member 7 that has a square cross-section. The bore 56 is slightly greater in size than the member 7, allowing for axially directed sliding movement of the sleeve 10 with respect to the member 7 during installation of the transition portion 8 into the sleeve 10 and also when both the portion 8 and the sleeve 10 are implanted with the sleeve 10 located between adjacent bone screws 15.

In the illustrated embodiment, the sleeve 10 further includes a plurality of compression grooves 62. Sleeves 10 according to the invention may include one, none or any desired number of grooves 62. Each groove 62 extends substantially uniformly about the sleeve 10 as illustrated in FIG. 7, being formed in the pairs of external surfaces 50, 52 of the sleeve 10. The groove or grooves 62 may be added as desired to advantageously increase a longitudinal compressibility of the sleeve 10 during installation between a pair of bone screws 15.

When the sleeve 10 is received about the central connection portion 8, the sleeve 10 completely surrounds the central portion 8 as illustrated in FIG. 8. It is noted that in addition to limiting the bendability of the central connection portion 8 and thus providing strength and stability to the assembly 1, the sleeve 10 also keeps scar tissue from growing into the portion 8 at the end 22 and apertures 28, thus eliminating the need for a sheath-like structure to be placed, adhered or otherwise applied to the central connection portion 8.

The dynamic connecting member assembly 1 cooperates with at least a pair of bone anchors, such as the polyaxial bone screws, generally 15 and cooperating closure structures 65 shown in FIG. 1, the assembly 1 being captured and fixed in place at the portions 6 and 7 by cooperation between the bone screws 15 and the closure structures 65. The sleeve 10 is sized and shaped to closely fit between pairs of bone screws 15 or other bone anchors or implants, cooperating with the central connection portion 8 to support adjacent vertebrae.

Because the members 6 and 7 are both solid and, as illustrated, either substantially cylindrical (member 6) or of other uniform cross-section (member 7), the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The solid portions 6 and 7 are particularly suited for use with polyaxial bone screws. For example, a spline capture connection polyaxial bone screw as described in U.S. Pat. No. 6,716,214 and incorporated by reference herein, may be used with longitudinal connecting member assemblies according to the invention.

The illustrated polyaxial bone screw 15 is particularly advantageous for use with assemblies according to the invention as the screw 15 includes a squared off seat and compression member combination that securely receives both cylindrical and bar-shaped longitudinal connecting members. With reference to FIGS. 1 and 8, the illustrated polyaxial bone screw assembly 15 includes a shank 74 that further includes a body 76 integral with an upper portion or capture structure 78; a receiver 80; and an independent retainer illustrated as an open collar-like retaining and articulating structure 82 and a compression member 84. The shank 74, the receiver 80, the retainer 82 and the compression member 84 preferably are assembled prior to implantation of the shank body 76 into a vertebra (not shown).

FIG. 1 further shows the closure structure 65 for compressing and biasing the longitudinal connecting member portion 6 or the portion 7 against the compression member 84 which presses against the shank upper portion 78 which biases the retainer 82 into fixed frictional contact with both the shank upper portion 78 and the receiver 80, so as to fix the portion 6 or the portion 7 relative to the vertebra (not shown). The receiver 80, the retainer 82 and the shank 74 cooperate in such a manner that the receiver 80 and the shank 74 can be secured at any of a plurality of angles, articulations or rotational alignments relative to one another and within a selected range of angles both from side to side and from front to rear, to enable flexible or articulated engagement of the receiver 80 with the shank 74 until both are locked or fixed relative to each other near an end of an implantation procedure.

The shank 74, best illustrated in FIGS. 1 and 5, is elongate, with the shank body 76 having a helically wound bone implantable thread 85 extending from near a neck 86 located adjacent to the upper portion 78 to a tip 88 of the body 76 and extending radially outwardly therefrom. During use, the body 76 utilizing the thread 85 for gripping and advancement is implanted into a vertebra (not shown) leading with the tip 88 and driven down into the vertebra with an installation or driving tool (not shown), so as to be implanted in the vertebra to near the neck 86. The shank 74 has an elongate axis of rotation generally identified by the reference letter C.

The neck 86 extends axially upwardly from the shank body 76. Further extending axially from the neck 86 is the shank upper portion or capture structure 78 that provides a connective or capture apparatus disposed at a distance from the thread 85 and thus at a distance from the vertebra (not shown) when the body 76 is implanted in such vertebra.

The shank upper portion 78 is configured for connecting the shank 74 to the receiver 80 and capturing the shank 74 in the receiver 80. The shank upper portion 78 has an outer, convex and substantially spherical surface 90 that extends outwardly and upwardly from the neck 86 and terminates at a curved top 92. The spherical surface 90 has an outer radius configured for sliding cooperation and ultimate frictional mating with a concave surface of the retainer 82 having a substantially similar radius. The spherical surface 90 is smooth, but it is foreseen that such surface may include a roughened or textured surface or surface finish, or may be scored, knurled, or the like, for enhancing frictional engagement with the retainer 82. A counter sunk drive feature 94 is formed in the top 92 (shown as a hexagonal aperture). In operation, a driving tool (not shown) engages the feature 94 for driving the shank body 76 into bone. The drive feature 94 may take a variety of tool-engaging forms and may include one or more apertures or imprints of various shapes, such as a pair of spaced apart apertures or a multi-lobular aperture, such as those sold under the trademark TORX, or the like. It is foreseen that in some embodiments, the bone screw shank upper portion may have an external tool engagement structure.

The illustrated shank 74 is cannulated, having a small central bore 95 extending an entire length of the shank 74 along the axis C, coaxial with the threaded body 76. The bore 95 has a first circular opening at the shank tip 88 and a second circular opening at the drive feature 94. The bore 95 provides a passage through the shank 74 interior for a length of wire (not shown) inserted into a vertebra (not shown) prior to the insertion of the shank body 76, the wire providing a guide for insertion of the shank body 76 into the vertebra.

To provide a biologically active interface with the bone, the threaded shank body 76 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$, tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The receiver 80 has a generally squared-off U-shaped appearance with a discontinuous partially cylindrical inner profile and a faceted outer profile. The receiver 80 includes a base 102 integral with a pair of upstanding arms 104 forming a cradle and defining a squared-off U-shaped channel 106 between the arms 104 with an upper opening 107 and a lower seat 108 having a width for receiving the bar-shaped portion 30 of the elastomeric member 7 or the rigid rod portion 6, for operably snugly receiving either of the members 6 and 7.

Each of the arms 104 has an interior surface 110 that defines the inner cylindrical profile and includes a partial helically wound guide and advancement structure 112. In the illustrated embodiment, the guide and advancement structure 112 is a partial helically wound interlocking flangeform configured to mate under rotation with a similar structure on the closure structure 65, as described more fully below. However, it is foreseen that the guide and advancement structure 112 could alternatively be a square-shaped thread, a buttress thread, a reverse angle thread or other thread like or non-thread like helically wound discontinuous advancement structure for operably guiding under rotation and advancing the closure structure 65 downward between the arms 104, as well as eventual torquing when the closure structure 65 abuts against the rigid rod portion 6 or the elastomeric bar 7.

Tool engaging apertures 114 are formed on or through surfaces of the arms 104 that may be used for holding the receiver 80 during assembly with the shank 74, the retainer 82 and the compression member 84 and also during the implantation of the shank body 76 into a vertebra (not shown). Furthermore, each of the arms 104 also includes a V-shaped or undercut tool engagement groove 116, formed on outer surfaces thereof which may be used for holding the receiver 80 with a holding tool (not shown) having projections that are received within the grooves 116 during implantation of the shank body 76 and/or during subsequent installation of the longitudinal connecting member assembly 1 and the closure structure 65. It is foreseen that tool receiving grooves or apertures may be configured in a variety of shapes and sizes and be disposed at other locations on the receiver arms 104.

On either side of the channel 106, the arms 104 of the receiver 80 include opposed planar surfaces 120 that cooperate with the opposed flat surfaces 46 and 48 of the sleeve 10 when the assembly 1 is operatively attached to the bone screws 15 as illustrated in FIG. 8. With reference to FIG. 1, communicating with and located beneath the channel 106 of the receiver 80 is a chamber or cavity 122 substantially defined by a partial inner spherical seating surface 124 of the base 102. The seating surface 124 is sized and shaped for slidable mating and eventual frictional engagement with the retainer 82, as described more fully below. The cavity 122 opens upwardly into the U-shaped channel 106 and downwardly to a bore 126 defined by a neck 128 that opens to a lower exterior 130 of the base 102. The bore 126 is coaxially aligned with respect to a rotational axis D of the receiver 80. The neck 128 and the associated bore 126 are sized and shaped to be smaller than an outer radial dimension of the open, uncompressed retainer 82, as will be discussed further below, so as to form a restriction at the location of the neck 128 relative to the retainer 82, to prevent the uncompressed retainer 82 from passing from the cavity 122 and out to the lower exterior 130 of the receiver 80 when the retainer 82 is seated and loaded.

The partially spherical and discontinuous or open retainer 82 that both retains and articulates is used to hold the spherically surfaced 90 upper portion 78 of the shank 74 within the receiver 80 and is also independently slidably and pivotally engageable with both the shank upper portion 78 at the surface 90 and the receiver 80 at the seating surface 124. The retainer 82 illustrated in FIGS. 1 and 8 has an operational central axis E that may be the same or different from the axis C associated with the shank 74, or the axis D associated with the receiver 80 when the shank upper portion 78 and the retainer 82 are installed within the receiver 80. The retainer 82 has a central channel or bore substantially defined by a discontinuous inner partially spherical surface 140 disposed between a top surface 142 and a bottom surface 144 of the retainer 82. The inner spherical surface 140 has a radius sized and shaped to cooperate with a radius of the substantially spherical surface 90 of the shank upper portion 78 such that the surface 140 slidingly and pivotally mates with the spherical surface 90. The surface 140 may include a roughening or surface finish to aid in frictional contact between the surface 140 and the surface 90, once a desired angle of articulation of the shank 74 with respect to the retainer 82 is reached.

The resilient retainer 82 includes first and second end surfaces, 146 and 147 disposed in spaced relation to one another and a discontinuous outer partially spherically shaped surface 150. Both end surfaces 146 and 147 are disposed substantially perpendicular to the top surface 142 and the bottom surface 144. A width of the space between the surfaces 146 and 147 is determined to provide adequate space for the retainer 82 to be pinched, with the surfaces 146 and 147 compressed toward one another to an almost touching or touching configuration, to an extent that the compressed retainer 82 is up or bottom loadable into the receiver cavity 122 through the bore 126 defined by the restrictive neck 128 while mounted on the neck 86 of the bone screw shank body 76. After passing through the bore 126 simultaneously with the shank upper portion 78, the retainer 82 expands or springs back to an original uncompressed, rounded or collar-like configuration of FIG. 1 once in the cavity 122. Once the resilient structure 82 returns to an original form, but now surrounding the spherical structure 78, the engaged structures 78 and 82 are then movable together within the cavity 122 to a variety of positions in which the surface 150 of the structure 82 is in slidable mating engagement with the seating surface 124 of the receiver 80.

The embodiment shown in FIGS. 1 and 8 illustrates the surfaces 146 and 147 as substantially parallel and vertical, however, it is foreseen that it may be desirable to orient the surfaces obliquely or at a slight angle depending upon the amount of compression desired during loading of the retainer 82 into the receiver 80. Also, other embodiments according to the invention, particularly smaller bone screw assemblies, may include retainers small enough to top load into the receiver channel upper opening 107, rather than loading through the receiver neck 128.

The compression member 84 is sized and shaped to be received by and uploaded into the receiver 80 at the neck 128. In operation, the member 84 is disposed between the rigid member 6 or the elastomeric member 7 and the upper portion 78 of the bone screw 74 as illustrated in FIG. 8. When the closure structure 65 presses upon the member 6 or the member 7, the member 6 or 7 operatively presses upon the compression member 84 that in turn presses upon the shank upper portion 78 that in turn presses against the retainer 82 that in turn presses against the seating surface 124 of the receiver 80, resulting in ultimate frictional engagement and locking the angular position of the bone screw shank 74 with respect to the receiver 80. The compression member 84 has an operational central axis F that is the same as the central axis D of the receiver 80. The compression member 84 has a central channel or through bore substantially defined by a an inner cylindrical surface 160 and an inner partially spherical surface 162 (shown in phantom in FIG. 8). The compression member through bore is sized and shaped to receive a driving tool (not shown) therethrough that engages the shank drive feature 94 when the shank is driven into bone. The surface 162 is sized and shaped to cooperate with the spherical surface 90 of the shank upper portion 78 such that the surface 162 slidingly and pivotally mates with the spherical surface 90. The surface 162 may include a roughening or surface finish to aid in frictional contact between the surface 162 and the surface 90, once a desired angle of articulation of the shank 74 with respect to the retainer 12 is reached.

The compression member 84 also includes a substantially planar top surface 164, a bottom surface 166 and an outer cylindrical surface 168. The cylindrical surface 168 is sized to be received within the interior cylindrical surface 110 defining the receiver 80 at the arms 104 and located between the guide and advancement structure 112 and the chamber 122 as best shown in FIG. 8. Thus, the compression member 84 ultimately seats on the shank upper portion 78 and is disposed at least partially in the channel 106 such that the compression member 84 top surface 164 substantially contacts the member 6 or the member 7 when the longitudinal connecting member assembly 1 is placed in the receiver 80 and the closure structure 65 is tightened therein.

With reference to FIGS. 1 and 8, the closure structure or closure top 65 can be any of a variety of different types of closure structures for use in conjunction with the present invention with suitable mating structure on the upstanding arms 104. In the embodiment shown, the closure top 65 is rotatably received between the spaced arms 104, but could be a slide-in closure structure. The illustrated closure structure 65 is substantially cylindrical and includes an outer helically wound guide and advancement structure 172 in the form of a flange form that operably joins with the guide and advancement structure 112 disposed on the arms 104 of the receiver 80. The flange form utilized in accordance with the present invention may take a variety of forms, including those described in applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 65 downward between the arms 104 and having such a nature as to resist splaying of the arms 104 when the closure structure 65 is advanced into the U-shaped channel 106. The illustrated closure structure 65 also includes a top surface 174 with an internal drive 176 in the form of an aperture that may be a hex drive, a star-shaped internal drive, for example, sold under the trademark TORX or other internal drives such as slotted, tri-wing, spanner, two or more apertures of various shapes, and the like. A driving tool (not shown) sized and shaped for engagement with the internal drive 176 is used for both rotatable engagement and, if needed, disengagement of the closure 65 from the arms 104. It is also foreseen that the closure structure 65 may alternatively include a break-off head designed to allow such a head to break from a base of the closure at a preselected torque, for example, 70 to 140 inch pounds. Such a closure structure would also include a base having an internal drive to be used for closure removal. A bottom surface 178 of the closure may be planar or include a point, points, a rim or roughening for engagement with the member 6 or the member 7 of the longitudinal connecting member assembly 1.

Prior to the polyaxial bone screw assembly 15 being placed in use according to the invention, the retainer 82 is first inserted about the neck 86 of the shank body 76 by inserting the shank tip 88 into the retainer through bore defined by the inner surface 140 and feeding the shank body 76 therethrough until the retainer 82 is located at the neck 86. Alternatively, in certain embodiments, the retainer 82 is placed near the neck 86 and the end surfaces 146 and 147 are pulled away from one another and pressed against and about the neck 86 until the surfaces 146 and 147 expand around the neck 86 and then spring back into a first position with the inner surface 140 disposed adjacent to the neck 86 and the top surface 142 facing toward the spherical surface 90 of the shank upper portion 78.

The compression member 84 is up or bottom loaded into the receiver 80 through the bore 126 with the top surface 164 facing the bore 126 and the cylindrical surface 168 moved upwardly through the neck 128. The compression member 84 may be placed on the shank upper portion 78 with and the spherical surface 162 seated on the surface 90 of the shank upper portion 78 and then uploaded simultaneously with the shank upper portion 78 and the retainer 82. The upper portion 78 and the connected structure 82 are then simultaneously up or bottom-loaded into the receiver cavity 122 by inserting the upper portion 78 through the neck 128 and into the cavity 122 and manually compressing the retainer 82 by pinching the surfaces 146 and 147 toward one another and inserting the neck 86 and the compressed retainer 82 into the bore 126 of the receiver 80. After the retainer 82 moves beyond the bore 126 and into the cavity 122, the compressive force is removed and the retainer 82 resiliently springs back and returns to the original ring-like or collar-like orientation, capturing the shank upper portion 78 within the receiver 80. Then, the shank body 76 is pulled downwardly away from the receiver 80, forcing the retainer 82 to temporarily expand about the spherical surface 90 of the shank upper portion 78 with the end surfaces 146 and 147 moving away from one another. Such an expansion of the retainer 82 allows the spherical surface 90 to slide into the retainer 82 until the outer surface 90 of the shank upper portion 78 is in sliding pivotal cooperation with the inner surface 140 of the retainer 82. The retainer 82 resiliently returns to the original ring-link orientation, with the spherical surface 140 capturing the shank upper portion 78 at the spherical surface 90, but allowing for pivotal, sliding movement or articulation of the retainer 82 with respect to the shank upper portion 78. Once the retainer 82 returns to the original orientation, both the connected structures 78 and 82 drop down to a seated position with the retainer 82 independently slidable with respect to both the shank upper portion 78 and the receiver 80, forming a multi- or compound articulation or joint between the shank 74 and the receiver 80. The compression member 84 may then be pressed downwardly and into full contact with the surface 90. It is noted that the receiver 80 may include an inner ledge, ridge or inwardly extending protrusion or protrusions to ensure that the compression member 84 does not slip out of the upper opening of the receiver 80.

The compression member 84, the retainer 82 and the attached shank upper portion 78 may then be manipulated into a substantially coaxial position in readiness for bone implantation. The assembly 15 is typically screwed into a bone, such as a vertebra (not shown), by rotation of the shank 74 using a driving tool (not shown) that operably drives and rotates the shank 74 by engagement thereof with the drive feature 94.

Typically, the receiver 80, the compression member 84, and the retainer 82 are assembled on the shank 74 before inserting the shank body 76 into a vertebra. However, in certain circumstances, such as when a small bone screw is utilized and the retainer is top loadable, the shank body 76 can be first partially implanted with the shank upper portion 78 extending proud to allow assembly with the receiver 80, followed by assembly with a top loaded retainer 12 and a top loaded compression member 84. Then the shank body 76 can be further driven into the vertebra.

The vertebra (not shown) may be pre-drilled to minimize stressing the bone and have a guide wire (not shown) inserted to provide a guide for the placement and angle of the shank 74 with respect to the vertebra. A further tap hole may be made using a tap with the guide wire as a guide. Then, the bone screw assembly 15 or the solitary shank 74, is threaded onto the guide wire utilizing the cannulation bore 95 by first threading the wire into the opening at the bottom 88 and then out of the top opening at the drive feature 94. The shank 74 is then driven into the vertebra using the wire as a placement guide. It is foreseen that the screws 15 and the longitudinal connecting member assembly 1 can be inserted in a percutaneous or minimally invasive surgical manner.

The sleeve 10 is typically cut to size by the surgeon for closely fitting between a pair of adjacent bone screw assemblies 15. The longitudinal connecting member assembly 1 that has been fabricated to include the rigid member 6 with the elastomeric member 7 molded thereto is then assembled with the sleeve 10 by inserting an end of either the member 6 or the member 7 into the bore 56 defined by the inner surfaces 58 of the outer sleeve 10. The sleeve 10 is moved into position over the central portion 8, thus covering the rod portion 24 and the member 7 connection portion 34.

With reference to FIG. 8, the longitudinal connecting member assembly 1 is eventually positioned in an open or percutaneous manner in cooperation with the at least two bone screw assemblies 15 with the sleeve 10 disposed between the two bone screw receivers 80 and a portion of the member 6 within one receiver 80 and a portion of the member 7 within the other receiver 80. A closure structure 65 is then inserted into and advanced between the arms 104 of each of the bone screw assemblies 15. The closure structure 65 is rotated, using a tool engaged with the inner drive 176 until a selected pressure is reached at which point the members 6 and 7 are each urged toward, but not completely seated on the lower seat 108. For example, about 80 to about 120 inch pounds pressure may be required for fixing each bone screw shank 74 with respect to the receiver 80.

As each closure structure 65 rotates and moves downwardly into the respective receiver 80, the bottom surface 178 presses against the longitudinal connecting member assembly member 6 or 7 and the structure 65 biases the member 6 or 7 downward into engagement with the compression member 84 that operably produces a frictional engagement between the member 84 and the shank surface 90 and also urges the shank upper portion 78 toward the retainer 82 and, in turn, the structure 82 toward the base 102 of the receiver 80, so as to frictionally seat the spherical surface 90 against the inner spherical surface 140 of the retainer 82 and the outer spherical surface 150 of the retainer 82 against the internal spherical seating surface 124 of the receiver 80, also fixing the shank 74 and the retainer 82 in a selected, rigid position relative to the receiver 80. At this time it is also possible for the retainer 82 to expand somewhat for an even tighter fit in the receiver cavity 122.

It is foreseen that an assembly 1 according to the invention may cooperate with an open receiver that is integral or fixed in position with respect to a bone screw shank or bone hook, or with a receiver having limited angular movement with respect to the shank, such as a hinged connection, also with or without other compression members or inserts for fixing the assembly 1, the receiver and/or the bone anchor in a desired position or orientation with respect to the cooperating vertebrae.

As indicated previously herein, as the closure structures 65 are rotated and then tightened against the members 6 and 7 within a pair of spaced bone screw receivers 80, such bone screw receivers 80 may be tilted or otherwise pressed toward one another, thereby compressing the sleeve 10. When the insertion and tightening tools are removed, the sleeve 10, pressing against facing surfaces 120 of the cooperating bone screw receivers 80, stretches and tensions the elastomeric member 7 that is part of the transition portion 8 that is disposed between such cooperating bone screw receivers 80. The assembly 1 is thus substantially dynamically loaded and oriented relative to the cooperating vertebra, providing relief (e.g., shock absorption) and protected movement with respect to flexion, extension, distraction and compressive forces placed on the assembly 1 and the two connected bone screws 15. The member 7 also allows the central portion 8 to twist or turn, providing relief for torsional stresses. The sleeve 10 limits such torsional movement as well as bending movement of the central connection portion 8, providing spinal support. Furthermore, because the sleeve 10 is compressed during installation, the sleeve advantageously allows for some protected extension or distraction of both the central connection portion 8 and the sleeve 10 as well as compression of the assembly 1 in cooperation with the central connection portion 8.

If removal of the assembly 1 from any of the bone screw assemblies 15 is necessary, or if it is desired to release the assembly 1 at a particular location, disassembly is accomplished by using the driving tool (not shown) that mates with the internal drive 176 on the closure structure 65 to rotate and remove the closure structure 65 from the cooperating receiver 80. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the member 6 or a solid bar with the same width as the member 7, utilizing the same receivers 80 and closure structures 65. Furthermore, it is noted that the members 6 and 7 may be elongate, allowing for connection of both rigid rod portions and/or elastomeric portions of the assembly 1 with additional bone screws or other bone anchors along a patient's spine. A connecting member assembly according to the invention may also include more than one transition portion 8 along a length thereof. Thus, such a connecting member may include various and alternating lengths of rigid and flexible support.

With reference to FIGS. 9-11, an alternative longitudinal connecting member assembly embodiment according to the invention, generally 201 includes a first rigid member 206, a second more flexible, elastomeric member 207 and a central, dynamic connection or transition portion or segment 208 disposed at and near a juncture of the members 206 and 207. The transition portion or segment 208 is receivable in a spacer or sleeve 210 with the sleeve 210 ultimately in position about the segment 208 when the assembly 201 is operatively assembled with at least a pair of bone screw assemblies 215 and 216 as illustrated in FIG. 8. Specifically, the connecting member assembly 201 is illustrated with the bone screw assembly 215 that is an open, monoaxial bone screw having a fixed shank 217 and cooperating with a closure top 218 substantially similar to the closure structure 65 previously described herein; and also shown with the bone screw assembly 216 that is a closed monoaxial bone screw having a fixed shank 219 and cooperating with a set screw 220.

The rigid member 206 is in the form of a rod identical or substantially similar to the rigid member 6 previously described herein with respect to the assembly 1. Thus, the member 206 includes an apertured portion 224 identical or substantially similar to the portion 24 previously described herein with respect to the rigid member 6. The elastomeric member 207 is substantially similar to the member 7 previously described herein with respect to the assembly 1 with the exception that the member 207 is in the form of a rod having substantially the same diameter as the rod 206. Similar to the member 7, the member 207 is molded with a connection portion 234 (similar to the portion 34 of the member 7) that flows into the apertures of the rod portion 224 during fabrication of the longitudinal connecting member assembly 201. The sleeve or spacer 210 is substantially similar to the spacer 10 previously described herein with respect to the assembly 1 with the exception that the sleeve 210 includes a central bore 256 having a circular cross-section that slidingly receives the cylindrical members 206 and 207.

As with the assembly 1, and as illustrated in FIG. 9, the assembly 201 readily cooperates with a wide variety of bone anchors and closures, and thus is not limited in use to the particular bone screws disclosed herein. In use, the longitudinal connecting member assembly 201 is factory fabricated to provide the flexible central transition portion 208. The sleeve 210 is slidable onto both the rigid portion 206 and the elastomeric portion 207, and placable about the central or transition portion 208. The sleeve 210 (as well as the sleeve 10 previously described herein) my be cut to the precise desired size by the surgeon. The connecting member assembly 201 is eventually positioned in an open or percutaneous manner in cooperation with the bone screws 215 and 216 with the sleeve 210 disposed between the two bone screws 216 and 217 and fitting closely therebetween. As with the assembly 1, closure structures or screws 218 and 220 are inserted into the bone screws and the sleeve 210 may be compressed by moving the bone screws 215 and 216 toward one another during tightening of the closure structures within the bone screw receivers. When the insertion and tightening tools are removed, the sleeve 210, pressing against facing surfaces of the adjacent cooperating bone screw receivers, stretches and tensions the member 207 that is part of the central connection portion 208. The assembly 201 is thus substantially dynamically loaded and oriented relative to the cooperating vertebra, providing relief (e.g., shock absorption) and protected movement with respect to flexion, extension, distraction and compressive forces placed on the assembly 201 and the two connected bone screws 215 and 216. The elastomeric member 207 at the central portion 208 allows the central portion 208 to twist or turn, providing relief for torsional stresses. The sleeve 210 limits such torsional movement as well as bending movement of the central connection/transition portion 208, providing spinal support. Furthermore, because the sleeve 210 is compressed during installation, the sleeve advantageously allows for some protected extension or distraction of both the central connection portion 208 and the sleeve 210 as well as compression of the assembly 201 in cooperation with the central connection portion 208.

It is to be understood that while certain forms of the present invention have been illustrated and described herein, it is not to be limited to the specific forms or arrangement of parts described and shown.

The invention claimed is:

1. A medical implant assembly comprising:
   a rigid segment attached to at least one of a first bone attachment structure or a second bone attachment structure;
   a flexible core member extending entirely through at least one of the first bone attachment structure or the second bone attachment structure, the flexible core member being pre-tensioned;
   a transition portion having an end portion and being at least partially disposed between the first bone attachment structure and the second bone attachment structure, the rigid segment and the flexible core member attached at the transition portion; and
   an outer flexible sleeve supporting at least a portion of the flexible core member, the outer flexible sleeve positioned entirely between the first bone attachment structure and the second bone attachment structure under compression and in any rotational position with respect to the transition portion when in an overlapping position with the end portion.

2. The medical implant assembly of claim 1, wherein the outer flexible sleeve at least partially covers the end portion of the transition portion.

3. The medical implant assembly of claim 1, wherein the outer flexible sleeve includes a through bore for receiving the flexible core member.

4. The medical implant assembly of claim 1, wherein the outer flexible sleeve has a cylindrical shape.

5. The medical implant assembly of claim 1, wherein the first bone attachment structure and the second bone attachment structure are each a bone anchor.

6. The medical implant assembly of claim 1, wherein the overlapping relationship includes the outer sleeve at least partially covering the end portion of the transition portion.

7. A medical implant assembly comprising:
   a rigid segment attached to at least one of a first bone attachment structure or a second bone attachment structure;
   a flexible core member extending entirely through at least one of the first bone attachment structure or the second bone attachment structure, the flexible core member being pre-tensioned;
   a transition portion being at least partially disposed between the first bone attachment structure and the second bone attachment structure, the rigid segment and the flexible core member attached at the transition portion; and
   an outer sleeve engaging the transition portion, the outer sleeve positioned between the first bone attachment structure and the second bone attachment structure under compression.

8. The medical implant assembly of claim 7, wherein an end portion of the transition portion is in an overlapping position with the outer sleeve.

9. The medical implant assembly of claim 7, wherein the rigid segment has a solid outer surface with at least one opening in an end portion and at least a portion of the flexible core member is disposed within the at least one opening.

10. A medical implant assembly comprising:
a rigid segment attached to at least one of a first bone attachment structure or a second bone attachment structure;
a flexible core member cooperating with the first bone attachment structure and the second bone attachment structure, the flexible core member held in tension;
a transition portion being at least partially disposed between the first bone attachment structure and the second bone attachment structure, the rigid segment and the flexible core member attached at the transition portion; and
an outer sleeve in an overlapping relationship with an end portion of the transition portion, the outer sleeve positioned between the first bone attachment structure and the second bone attachment structure under compression.

11. The medical implant assembly of claim 10, wherein the outer sleeve includes a through bore for receiving the flexible core member.

* * * * *